United States Patent [19]

Royce

[11] Patent Number: 5,403,593
[45] Date of Patent: Apr. 4, 1995

[54] MELT GRANULATED COMPOSITIONS FOR PREPARING SUSTAINED RELEASE DOSAGE FORMS

[75] Inventor: Alan E. Royce, Effort, Pa.

[73] Assignee: Sandoz Ltd., Basel, Switzerland

[21] Appl. No.: 860,920

[22] Filed: Mar. 31, 1992

Related U.S. Application Data

[63] Continuation of Ser. No. 664,195, Mar. 4, 1991, abandoned.

[51] Int. Cl.$^6$ .............................................. A61K 9/14
[52] U.S. Cl. .................................. 424/489; 424/480; 424/498; 424/488
[58] Field of Search ............... 424/489, 480, 476, 464, 424/469

[56] References Cited

U.S. PATENT DOCUMENTS

| | | | |
|---|---|---|---|
| 3,147,187 | 9/1964 | Playfair | 167/82 |
| 3,870,790 | 3/1975 | Lowey | 424/469 |
| 4,140,755 | 2/1979 | Sheth et al. | 424/21 |
| 4,389,393 | 6/1983 | Schor | 424/480 |
| 4,774,074 | 9/1988 | Snipes | 424/19 |
| 4,828,836 | 5/1989 | Elger | 424/464 |
| 4,849,229 | 7/1989 | Gaylord et al. | 424/468 |
| 4,882,167 | 11/1989 | Jang | 424/468 |
| 5,023,108 | 6/1991 | Bagaria | 424/476 |

OTHER PUBLICATIONS

*Pharmaceutical Dosage Forms: Tablets*, vol. 1 (2nd Ed.) ed. by Lieberman et al., Marcel Dekker Inc. (1989), p. 150.

Flanders, P. et al., The Control of Drug Release from Conventional Melt Granulation Matrices, Drug Devel. and Ind. Pharm., 13 (6), 1001–1022 (1987).

Kopcha, M. et al. Development and In-Vitro Characterization of Sustained -Release Acetaminophen Tablets, Phar. Res., 4, Suppl S27 (1987).

McTaggart et al., "The evaluation of formulation and processing conditions of a melt granulation process," *International Journal of Pharmaceutics*, 19 (1984) 139–148.

Pataki et al., "Rolling Bed Granulation With Local Melt Forming, " Proc. Conf. Appl. Chem. Unit Oper. Processes, 3(4):258–270 (1983).

Rubinstein et al., Drug Development and Industrial Pharmacy, 6(5), 451–473 (1980).

G Shah, et al., "Polyethylene Glycol as a Binder for Tablets," *Journal of Pharmaceutical Sciences* 66, No. 11, Nov. 1977, 1551–1552.

Rubinstein, M., "A New Granulation Method for Compressed Tablets," *Pharm. Pharmac.*, 28, Suppl. 67P (1976).

*Primary Examiner*—Thurman K. Page
*Assistant Examiner*—William E. Benston, Jr.
*Attorney, Agent, or Firm*—Robert S. Honor; Richard E. Vila; Diane E. Furman

[57] ABSTRACT

Therapeutically active sustained release dosage forms are described which are prepared from compositions which comprise (A) a hydrophilic cellulose ether polymer or mixtures thereof as a binder matrix material, (B) a granulating medium selected from the group consisting of a lipid component, polyethylene glycol polymers, and mixtures thereof, said granulating medium having a melting range higher than about 30° C., and (C) a therapeutically active medicament, said components being in melt association. The compositions are prepared by a melt granulation process.

23 Claims, 2 Drawing Sheets

MELT GRANULATED COMPOSITIONS FOR PREPARING SUSTAINED RELEASE DOSAGE FORMS

This is a continuation of application Ser. No. 07/664,195, filed Mar. 4, 1991, which is now abandoned.

FIELD OF THE INVENTION

This invention relates to compositions comprising a therapeutically active medicament which are formed into solid, shaped unit dosage forms. More particularly, the invention relates to melt granulated compositions comprising hydrophilic cellulose ether polymers as a carrier base material, binder or matrix, and to sustained release dosage forms prepared from such compositions. Compositions and dosage forms comprising the medicaments, spirapril or clemastine fumarate, are described.

BACKGROUND OF THE INVENTION

In order to prepare solid, shaped dosage forms from fine particles or powders, it is generally necessary to process the powders in a manner to improve their flowability, cohesiveness and other characteristics which will enable the resulting material to be fabricated by conventional processes such as tableting, encapsulation, molding, etc. into a satisfactory unit form that can suitably deliver an agent into the environment of use.

Various processes are well-known in the pharmaceutical art for modifying starting powders or other particulate materials, in which typically the powders are gathered together with a binder material into larger permanent free-flowing agglomerates or granules referred to collectively as a "granulation."

For example, solvent-assisted "wet" granulation processes are generally characterized in that the powders are combined with a binder material and moistened with water or an organic solvent under conditions to result in formation of a wet granulated mass from which the solvent must then be evaporated. Such processes while widely employed have certain recognized limitations arising from the use when necessary of nonaqueous solvents which are environmentally deleterious, and furthermore may not be readily adaptable in connection with moisture sensitive medicaments.

In particular, formulations comprising hydrophilic cellulose ether polymers as a carrier base or matrix material, can present problems in formulation by aqueous wet granulation means. Alternative "dry granulation" processes, which often depend on fairly complicated milling schemes to produce a suitable granulation, also have acknowledged disadvantages in relation to such formulations. Nor are the finely divided cellulose ether particles in higher concentrations readily suitable in a direct compression process.

Such cellulose ether-based formulations, as exemplified in U.S. Pat. Nos. 3,065,143, 3,870,790, 4,226,849, 4,357,469, 4,389,393, 4,540,566, 4,795,327 and 4,849,229 (all assigned to Forest Laboratories, Inc.), have been found useful in particular to prepare sustained release dosage forms.

In such dosage forms the hydrophilic cellulose ether polymer typically functions as a binder or matrix system to regulate release of components of the dosage form. When introduced into the environment, the polymer partially hydrates where directly exposed to water to form a gelatinous layer. This original protective gel layer, once formed, permits additional fluid to penetrate into the interior of the dosage device. As the outer gel layer begins to fully hydrate and dissolve, a new layer replaces it which optimally is sufficiently strong to continue to retard outward diffusion and thus maintain the sustained release features of the dosage form, for the desired length of time.

The art has long recognized the benefits of achieving a long-lasting and regular incremental release of a therapeutic agent upon administration, and accordingly it has been a continuing objective to provide improved compositions and processes for preparing such cellulose ether-based sustained release dosage forms.

Certain melt granulation techniques have been developed in the art which in general comprise the use of room temperature solid or semi-solid materials having a relatively low softening or melting range to promote granulation of powdered or other materials, in the substantial absence of added water or other liquid solvents. The low melting solids, when heated to a temperature at or near or the melting range, liquify to act as a binder or granulating medium which spreads itself over the surface of powdered or particulate materials with which it is associated, and on cooling, forms a solid granulated mass in which the powder or particulate starting materials are bound. The resulting melt granulation can then be provided to a tablet press, mold, or encapsulator, etc., for preparing the dosage form, see, e.g., *Pharmaceutical Dosage Forms: Tablets*, Vol. 1 (2d Ed.) ed. by Lieberman et al., Marcel Dekker Inc. (1989), pp. 148–151.

It will be evident that a melt granulation process, by dispensing with wetting and drying steps, as well as facilitating a virtually "one-pot" granulating technique, can potentially provide significant improvements over other granulation methods, and that such a process and compositions, where these can be applied, would be highly useful to the art.

It has now been discovered and is an aspect of this invention that hydrophilic cellulose ether-based compositions, particularly high concentration cellulose compositions (e.g. 20 wt. % or higher) may be prepared by a melt granulation process.

The compositions may be conveniently tableted or otherwise manufactured into shaped dosage forms comprising a therapeutic agent, especially sustained release dosage forms.

SUMMARY OF THE INVENTION

The dosage forms of the invention are prepared from compositions which comprise:

(A) 5 to 90 wt. % of a hydrophilic cellulose ether polymer, or mixtures thereof, (B) 5 to 50 wt. % of a granulating medium selected from the group consisting of a lipid component, ethylene oxide polymers, and mixtures thereof, said granulating medium having a melting range above about 30° C., and (C) a therapeutically active medicament, the above components being in melt association.

Preferably said compositions comprise the hydrophilic cellulose ether component in an amount above about 20 wt. %.

The compositions of the invention are prepared by a melt granulation process, in the substantial absence of added liquid solvents.

It has been found that a therapeutically active medicament or agent and additional excipients as desired can readily be dispersed within the compositions of the invention, and that the compositions can be formed into satisfactory dosage forms by conventional means, and can effect sustained release of the agent into the environment.

DETAILED DESCRIPTION

Figure 1:
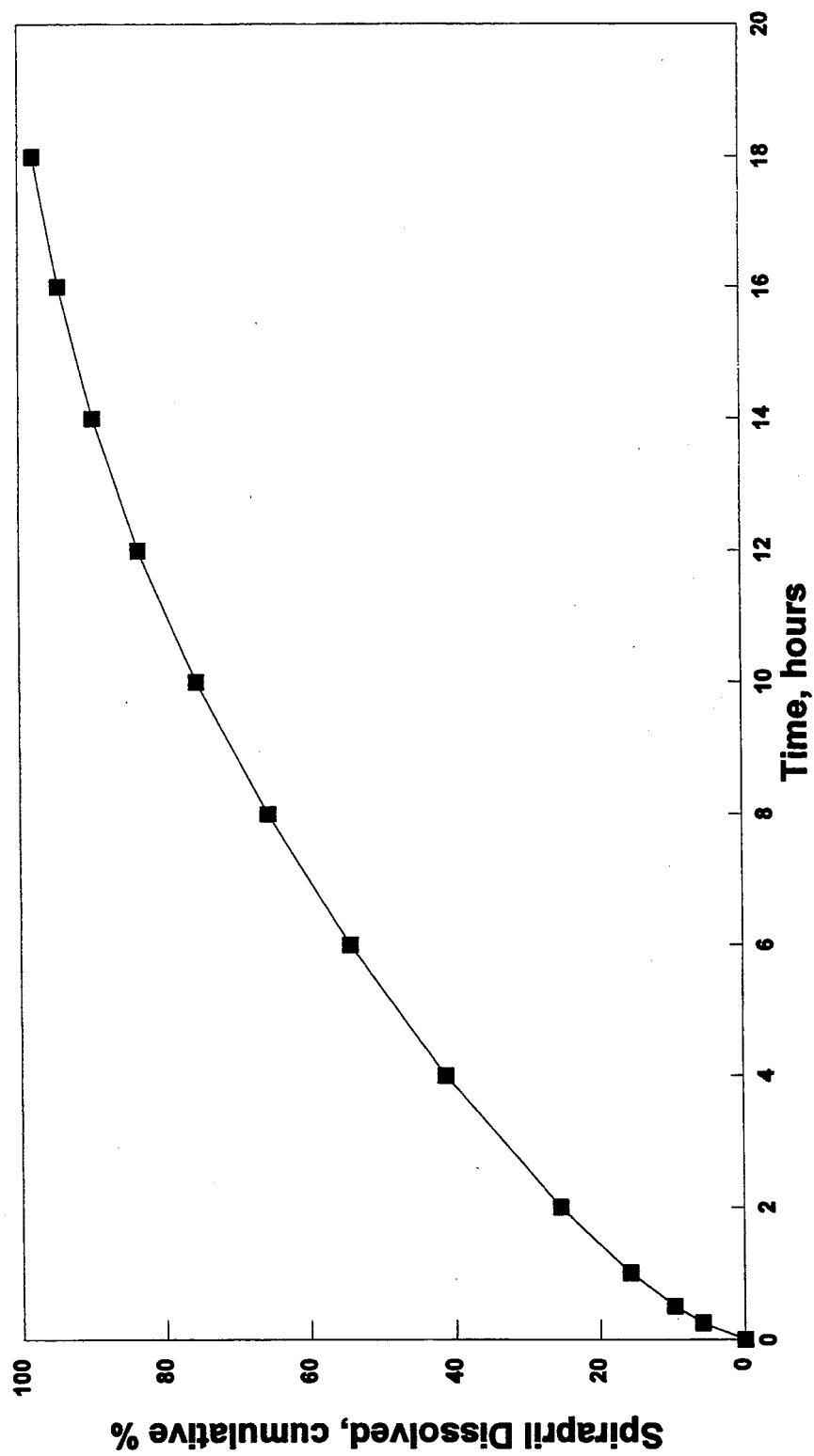
FIGS. 1 and 2 are graphs depicting the cumulative amount of the medicaments, spirapril hydrochloride or clemastine fumarate, respectively, dispensed over a prolonged period of time by dosage forms prepared from compositions of the invention.

Component (A) of the compositions of the invention comprises one or more hydrophilic cellulose ether polymers.

The hydrophilic cellulose polymers are well-known and are commercially available under several tradenames. The grades available under a given trade name represent variations in composition and molecular weight. For example, commercially available hydroxypropyl methylcellulose (HPMC) comprises a series of compounds (Methocel E,F,J and K, all formerly designated as versions of Methocel HG, of The Dow Chemical Co. and Metolose SH of Shin-Etsu, Ltd.) each having a different chemical composition, within a methoxyl content range of about 16.5 to 30 wt. % and a hydroxypropoxyl content range of about 4 to 32 wt. %, and each being available in various viscosity grades based on the viscosity of a 2% aqueous solution thereof at 20° C.

Particularly useful in the present invention are the relatively high viscosity grades of HPMC, e.g., the 4,000 cps grades of Methocel E and Metolose 60 SH; the 4,000 cps grade of Methocel F and Metolose 65 SH; the 5,000, 12,000, 20,000 and 75,000 cps viscosity grades of Methocel J; the 4,000, 15,000 and 100,000 cps viscosity grades of Methocel K; and the 4,000, 15,000, and 39,000 grades of Metolose 90 SH.

Specific examples of HPMC which can be employed in preparing sustained release formulations comprise Methocel K100LV, K4M, K15M, K100M, E4M, and E10M.

For example, Methocel K100LV is a 100 cps grade, Methocel K4M a 4,000 cps grade, K15M a 15,000 cps grade, and K100M a 100,000 cps grade of HPMC, each having a 19-24 wt. % methoxyl content and a 7-12 wt. % hydroxypropoxyl content.

Methocel E4M is a 4000 cps grade of HPMC having a 28-30 wt. % methoxyl content, and a 7-12 wt. % hydroxypropoxyl content.

See, e.g., *Formulating for Controlled Release with METHOCEL Cellulose Ethers*, The Dow Chemical Company (1987).

Preferred among the foregoing HPMC polymers are Methocel K15M and K100M.

Examples of methylcellulose polymers useful in the invention comprise Methocel A, formerly designated as Methocel MC, of The Dow Chemical Co., and Metolose SM of Shin-Etsu, Ltd., having a methoxyl content of about 27.5-31.5 wt. %.

Particularly preferred are the higher viscosity grades including the 4,000 and 15,000 cps viscosity grades of Methocel A and Metolose SM, and the 4,000 cps viscosity grade Methocel MC now designated as Methocel A4M.

Specific examples of suitable methylcellulose polymers comprise Methocel A15LV, Methocel A4C, Methocel A15C and Methocel A4M of the Dow Chemical Co. (see, e.g., *METHOCEL Cellulose Ethers: Technical Handbook*, The Dow Chemical Co,. c. 1988).

The foregoing HPMC and methylcellulose polymers can be used individually or in combination, including combinations of HPMC and methylcellulose, in the compositions of the invention.

Other potentially suitable hydrophilic cellulose ether polymers comprise hydroxypropylcellulose, hydroxyethylcellulose, sodiumcarboxymethylcellulose, carboxypolymethylene (Carbopol-Cabot Corp.), carboxymethylhydroxyethylcellulose, etc.

Of course, it will be evident that any of the foregoing cellulose ether polymers which is employed for a pharmaceutical use shall be pharmaceutically accceptable and have been approved for the particular use intended.

Component (B) of the compositions of the invention comprises a granulating medium which is selected from the group consisting of a lipid component, ethylene oxide polymers, and mixtures thereof, said medium having a melting range above about 30° C.

Preferably, the lowest melting component of the granulating medium has a melting range above about 40° C. The granulating medium preferably has a melting range within the range of about 50° to 100° C, and more preferably within the range of about 60°-70° C.

The term "lipid component" shall be understood to refer to lipid and lipid-like materials, including fatty esters, fatty acids and salts thereof, fatty alcohols, fatty amines, fatty amides, glycerides, glycolipids, steroids, natural and synthetic waxes, and mixtures thereof.

A preferred such component comprises glyceryl esters of fatty acids.

A particularly suitable material is glyceryl palmitostearate, such as that which is commercially available from Gattefosse Corp. (Elmsford, N.Y.) under the tradename, "Precirol®". Precirol ATO-5, for example, which comprises a mixture of mono, di and tri-glycerides, is in powder form at room temperature and has a melting range of 52°-55° C.

Other representative glyceryl esters comprise triglyceryl ester, glyceryl distearate, glyceryl tristearate, glyceryl monostearate, glyceryl dipalmitate, glyceryl tripalmitate, glyceryl monolaurate, glyceryl dodecosanoate, glyceryl tridecosanoate, glyceryl monodecosanoate, glyceryl monocaprate, glyceryl dicaprate, glyceryl tricaprate, glyceryl monomyristate, glyceryl dimyristate, glyceryl trimyristate, glyceryl monodecanoate, glyceryl didecosanoate, glyceryl tridecosanoate.

The fatty acids are preferably selected from fatty acids having 12 to 28 carbons, e.g., stearic acid, palmitic acid, lauric acid, eleostearic acid, etc.

The fatty alcohols are preferably compounds having from 16 to 44 carbons, e.g., stearic alcohol, palmitol, etc.

Suitable fatty amines are those having 13 to 45 carbons, and preferred fatty amides contain 11 to 45 carbons.

The lipid component may also comprise monoglycerides, diglycerides, triglycerides, glycolipids, steroids and organic salts of fatty acids having from 12 to 29 carbons. Examples thereof comprise stearin, palmitin, castor wax, lecithin, hydrogenated cottonseed oil, hydrogenated tallow, magnesium stearate and calcium and aluminum salts of palmitic and other fatty acids.

Examples of suitable waxes comprise paraffin wax, beeswax, carauba, jojoba, microcrystalline, palm, spermaceti, wool wax and other room temperature-solid hydrocarbon waxes.

A further suitable granulating component is a polymer of ethylene oxide. Polyethylene glycol (PEG), which is most preferred, has the generalized formula HO—(CH$_2$CH$_2$O)$_n$—H, wherein n represents the average number of oxyethylene groups. PEG in its commercial forms generally has a designation corresponding to the average molecular weight of the polymer. PEG having a molecular weight of about 4,000 to 6,000 is available as a fine powder, PEG 8000 as a waxy solid.

While any of the commercially available forms of PEG which have a melting range above about 30° C., i.e. those having an average molecular weight of at least about 900, is potentially suitable to prepare formulations of the invention, depending on the ultimate dosage form to be prepared, the preferred PEG polymers for use in the present invention comprise those having an average molecular weight of about 3000 to about 9000, e.g., CARBOWAX ® 3350, 4600 or 8000 (Union Carbide), the latter being most preferred.

The following preferred CARBOWAX ® polymers have the indicated melting ranges:

| CARBOWAX$^R$ | Melting Range (°C.) |
|---|---|
| PEG 3350 | 54–58 |
| PEG 4600 | 57–61 |
| PEG 8000 | 60–63 |

("*CARBOWAX ® Polyethylene Glycols: Product Information Bulletin,*" Union Carbide, 1986.)

Also potentially suitable as equivalent materials in the invention are other polyether glycols such as polypropylene glycol, and polyethylene glycol esters or acids, as well as polyoxypropylene and polyethylene oxide, copolymers thereof, and mixtures of the foregoing.

In a preferred embodiment of the compositions of the invention, the granulating medium comprises from about 0 to 30 wt. % (based on the total formulation) of the lipid component and 0 to 30 wt. % (based on the total formulation) of ethylene oxide polymer.

The compositions of the invention may in addition also optionally include various other excipients such as binders, diluents, disintegrants, etc. and minor amounts of lubricants, etc. well-known to the art.

Examples of optional diluent or binder materials include lactose, starches, sodium alginate, dicalcium phosphate hydrate, sugars, acacia, agar, calcium carrageenan, alginic acid, algin, agarose powder, microcrystalline cellulose, collagen, colloidal magnesium silicate, colloidal silicon dioxide, pectin, gelatin, calcium sulfate, ethyl cellulose, polyacrylates, etc.

Examples of lubricants include talc, colloidal silicon dioxide, stearic acid, metallic stearates, hydrogenated vegetable oils, corn starch, polyethylene glycols, sodium benzoate and sodium acetate. The granulating medium to an extent also acts as a lubricant in the composition. Preferably, a combination of talc and silicon dioxide is provided in an amount of about about 1–2 wt. % (based on the total composition).

Other optional components comprise colorants, sweeteners, and the like.

Coatings may also be applied to the dosage forms of the invention where appropriate, provided these are not incompatible with the desired sustained release effect.

The compositions of the invention are prepared by a melt granulation process.

The granulating medium, as previously indicated, comprises a material selected from the group consisting of a lipid component, ethylene oxide polymers, and mixtures thereof.

In order to carry out the melt granulation process of the invention, the melt granulating medium is heated to a temperature at which the medium is at least partially in a molten state.

Typically, heat is applied until molten regions are visibly formed within the granulating medium, indicating that the temperature of at least a part of the medium is within the melting range. In the absence of further application of heat, such molten regions may tend to enlarge to result in substantially complete conversion of the medium to the molten state.

Additionally, if the granulating medium comprises components having non-overlapping or partially overlapping melting ranges, it may be sufficient depending on the formulation, to heat to a temperature confined to the non-overlapping portion of the lower melting range, since the lower melting component when molten can serve to bind the remaining components of the granulating medium as well as the other components of the formulation.

As the granulating medium is heated and becomes molten, it forms liquid bridges between the particles of the composition which change to solid bonds upon cooling. A solid mass is thereby formed in which the granulating medium and the remaining components of the composition are closely bound together, forming agglomerations or granules. The term "melt association" employed herein refers to the bonding relationship among the components of the compositions of the invention which results from the cooling of a molten granulating component in a melt granulation process.

Said melt granulation process is carried out prior to fabrication of the dosage form by tableting, molding, or the like.

Preferably, the granulating medium is dry-blended with the cellulose ether component, the therapeutic agent and any other excipients (e.g., a solid diluent such as lactose) prior to heating. Alternatively, the granulating medium can be pre-heated to at least a softened state, and then combined with other components of the dosage form, including the therapeutic agent, and heat may be continued to be supplied to the resulting composition, as necessary, to carry out the melt granulation.

It will be within the skill of the worker in the art to devise techniques for ordering the heating and mixing of the various constituents of the compositions of the invention to result in the formation of a suitable melt granulation.

The compositions are maintained at an elevated temperature for a time sufficient to substantially completely liquify the composition of the invention.

The resulting composition is then cooled or allowed to cool, to room temperature.

The composition, as it liquifies and cools, is preferably blended or plowed on a continuous or semi-continuous basis to facilitate formation of a homogenous granulation in which the powder or particulate matter is well dispersed.

In the practice of the invention, heat may be applied by means of steam heat in a jacketed bowl equipped with blending means. For initial cooling, cold water may then be circulated through the jacketed bowl until the temperature drops below the melting range. The solidified material may then be recovered, optionally sized, and allowed to cool to room temperature.

As an alternative technique for preparing the melt granulated compositions of the invention, the molten granulating medium may be sprayed on a bed, which is preferably fluidized, comprising the remaining components of the compositions of the invention, e.g., the cellulose, therapeutic agent, and other excipients, under suitable conditions to form a melt granulation medium.

The recovered melt granulation can therefore be screened if necessary, and minor amounts of additional excipients, such as lubricants, may be added.

The resulting formulation is therafter compressed, molded, encapsulated or otherwise employed to result in formation of a unit dosage form.

A preferred composition providing dosage forms having sustained release characteristics comprises:
(A) 20 to 60 wt. % of hydrophilic cellulose ether polymer or mixtures thereof, and
(B) 5 to 30 wt. % of a granulating medium comprising:
  (i) 0 to 30 wt. % of a lipid component, and (wt. % based on total composition),
  (ii) 0 to 30 wt. % of ethylene oxide polymer. (wt. % based on total composition).

An even more preferred composition of the invention comprises:
(A) 30 to 40 wt. % of hydrophilic cellulose ether polymer or mixtures thereof, and
(B) 15 to 30 wt. % of a granulating medium comprising:
  (i) 5 to 20 wt. % of a lipid component (wt. % based on total composition),
  (ii) 5 to 20 wt. % of ethylene oxide polymer (wt. % based on total composition).

In the foregoing embodiment, most preferably, the lipid component (i) and the ethylene oxide polymer component (ii) respectively comprise 0 to 10 wt. %, based on the total composition.

In the above compositions, the cellulose ether polymer is preferably hydroxypropylmethylcellulose, more preferably HPMC having a methoxyl content of about 19–24 wt. % and a hydroxypropoxyl content of about 7–12 wt. %, especially, Methocel K15M or K100M.

The lipid component preferably is selected from glyceryl esters of fatty acids, and most preferably comprises glycerylpalmitostearate, such as is available under the tradename, "Precirol ®," (Gattefosse).

The ethylene oxide polymer is preferably selected from polyethylene glycols, and more is preferably selected from polyethylene glycols having a molecular weight of about 3,000 to about 9000, polyethylene glycol 8000 being most preferred.

The resulting formulations have satisfactory flowability and compression properties.

Dosage forms may be made by conventional compression tableting techniques using a tablet press, by molding methods, such as compression molding, by encapsulation (e.g., using a dosator encapsulator or tamper/disc encapsulator), or by other means known to the art.

The hardness of compressed tablets prepared from compositions of the invention over the entire range is satisfactory, generally ranging from about 4 to about 8.5 kp.

The term "therapeutically active medicament" or "therapeutic agent" or includes any physiologically or pharmacologically active substance that produces a local or Systemic effect(s) in animals, which include warm-blooded mammals, humans, primates, etc.

The term "physiological" as used herein denotes the administration of a drug to produce normal levels and functions. The term "pharmacological" denotes variations in response to the amount of drug administered to the host. The dosage forms of the invention have found a particular use as vehicles for various human and animal drugs, particularly for the oral administration thereof, although other systems as well, including systems such as buccal, implant, nose, artificial gland, rectum, cervical, intrauterine, occular, arterial, venous, ear and the like, may be manufactured according to the process of the invention.

The medicaments that can be delivered include inorganic and organic drugs, without limitation, drugs that act on the central nervous system, cardiovascular drugs, endocrine drugs, drugs for metabolic disorders, immunologic drugs, and drugs for treatment of allergies and infectious diseases. More particularly, such drugs may comprise depressants, hypnotics, sedatives, psychic energizers, tranquilizers, anti-hypertensives, anticonvulsants, muscle relaxants, antiparkinson agents, analgesics, anti-inflammatory, local anesthetics, muscle contractants, anti-microbials, anti-malarials, hormonal agents, contraceptives, sympathomimetics, diuretics, anti-parasitics, neoplastics, hypoglycemics, ophthalmics, electrolytes, diagnostic agents, and the like.

Compositions according to the invention may be prepared which comprise spirapril, its hydrates, or pharmaceutically acceptable salts thereof. Spirapril hydrochloride, i.e. (1) 1,4-Di-thia-7-azaspirol[4.4]nonane-8- carboxylic acid, 7-[2-[[1-(ethoxycarbonyl)-3-phenylpropyl]- amino]-1-oxopropyl]-monohydrochloride,-[8S-[7[R*(R*), 8R*]]; (2) (8S)-7[(S)-N-[(S)-1-Carboxy-3-phenylpropyl]alanyl]-1,4- dithia-7-azaspiro[4,4]-nonane-8-carboxylic acid, 1-ethyl ester, monohydrochloride, has activity as a cardiovascular drug, e.g., as an angiotensis converter (CAS-94841-17-5; CAS-83647-97-6).

Compositions according to the invention may also be prepared which comprise clemastine in free base form, or in a pharmaceutically acceptable acid addition salt form.

Clemastine fumarate, i.e., (1) Pyrrolidone, 2-[2-[1-(4-chlorophenyl)-1-phenylethoxy]ethyl]-1-methyl-, [R-(R*,R*)]-, (E)-2-butenedioate; (2) (+)-(2R)-2-[2-[[(R)-p-Chloro-α-methyl-α-phenylbenzyl]-oxy]ethyl]-1-methylpyrrolidone fumarate, is a colorless to faintly yellow, practically odorless, crystalline powder. It belongs to the benzhydryl ether group of antihistaminic compounds and has activity as an $H_1$-receptor antagonist (CAS 14976-57-9; CAS-15686-51-8).

The following examples are merely intended to illustrate the invention and are not limitative thereof. Unless otherwise expressly indicated the chemical substances used are in the National Formulary or the U.S. Pharmacopeia.

EXAMPLE 1

An oral dosage form comprising spirapril hydrochloride is prepared in a batch size of 40,000 tablets.

(a) 1.02 kg. of spirapril is combined with 2.65 kg. of lactose (anhydrous) in a jacketed mixer (Collette Gral Bowl), and blended for 2 minutes at low speed without choppers.

(b) To the resulting composition are added 0.8 kg. each of glycerylpalmitostearate (Precirol ® ATO5, Gattefosse) passed through a 14 mesh screen and anhydrous polyethylene glycol 8000 (Carbowax ®), and 2.40 kg. of hydroxypropylmethylcellulose 2208 (Methocel K15M Premium), to form a composition which is blended without choppers for 4 minutes at low speed. Blending is continued while steam heating is applied to the jacketed bowl for about 10–15 minutes until the temperature of the composition is about 65° C. The steam is then removed, and blending is continued until granulation is substantially complete.

Cold water is circulated through the jacketed bowl and plowing with choppers is continued at low activation until the composition is cooled to about 50° C. The composition is removed to paper lined trays and allowed to cool to room temperature, then sized by passing through a Frewitt 14-mesh screen using an oscillating granulator at medium speed.

The loss on drying (L.O.D.) of the granulation, determined by using a Compu-Trac moisture analyzer set at 90° C., is 0.96%.

Bulk density is 0.43 g/ml. Tap density is 0.51 g/ml.

The particle size distribution of the granulation is determined by transferring 100 g. of the granulation to a Cenco-Meinzer Sieve Shaker employing the below-indicated mesh sizes. The shaker is operated for 5 minutes and the results are as follows:

| Mesh Size | Grams Retained |
| --- | --- |
| 20 | 2.2 |
| 40 | 23.8 |
| 60 | 31.8 |
| 80 | 15.6 |
| 100 | 6.5 |
| 200 | 14.0 |
| Pan | 4.2 |
| Total | 98.1 | c) 0.12 kg. of talc and 0.02 kg. of colloidal silicon dioxide which have been passed through 60-mesh bolting cloth are then added. The mixture is blended for about 30 seconds at low speed without choppers, and 0.02 kg. of magnesium stearate is then added, and blending is continued for an additional 30 seconds.

(d) The resulting composition is charged for tableting to a Manesty Beta Press having an 8 mm. die head.

The recovered tablets are dedusted using a 14-mesh screen with a vacuum. The resulting tablets are about 195 mg. and have an off-white color. Each tablet comprises about 25.5 mg. of spirapril.

Hardness on a Heberlein (Schleuniger) Hardness Tester is 4–5.5 kg, and friability on a Hoffman-Laroche Friabilator at 25 rpm for 4 minutes is 0.02%.

EXAMPLE 2

An oral dosage form comprising clemastine fumarate is prepared in a batch size of 500,000 tablets.

(a) 1.34 kg. of clemastine fumarate (available from Sandoz Pharmaceuticals Corp. under the tradename Tavist ®) is combined with 43.12 kg. of lactose (anhydrous) in a jacketed mixer (Collette Gral Bowl), and blended for 1 minute at low speed without choppers and 1 minute at high speed without choppers.

(b) To the resulting composition are added 4.50 kg. of glycerylpalmitostearate (Precirol ® ATO5) passed through a 20 mesh screen, 9.00 kg. polyethylene glycol 8000 (Carbowax ®), and 27.00 kg. of hydroxypropyl methylcellulose 2208 (Methocel K15M Premium, Dow), to form a composition which is blended for 2 minutes at low speed without choppers. Blending is continued while steam heating is applied to the jacketed bowl until the temperature of the composition is about 65° C. The steam is removed, and blending is continued until granulation is substantially complete.

Cold water is then circulated through the jacketed bowl and plowing is continued at low speed with choppers at low activation until the composition is cooled to about 50° C. The composition is then sized by passing through a Frewitt 12-mesh screen using an oscillating granulator at medium speed.

The L.O.D. of the granulation, determined by using a Compu-Trac moisture analyzer set at 90° C., is 1.21.

The bulk density is 0.60 cc/ml. The tap density is 0.77 cc/ml.

(c) To the mixer are added 2.70 kg. of talc and 0.54 kg. of colloidal silicon dioxide which have been passed through 60-mesh bolting cloth. The resulting mixture is blended for about 30 seconds at low speed without choppers, and 1.80 kg. of stearic acid is then added, and blending is continued for an additional 30 seconds.

The particle size distribution of the granulated composition is determined by transferring 100 g. of the granulation to a Cenco-Meinzer Sieve Shaker employing the below-indicated mesh sizes. The shaker is operated for 5 minutes at setting 5 and the results are as follows:

| Mesh Size | Grams Retained |
| --- | --- |
| 20 | 3.1 |
| 40 | 14.1 |
| 60 | 9.2 |
| 80 | 7.5 |
| 100 | 7.5 |
| 200 | 36.8 |
| Pan | 21.7 |
| Total | 100 |

(d) The resulting composition is charged for tableting to a Korsch Press having a 4×8 mm. die head.

The recovered tablets are dedusted using a vacuum vibrator. The tablets are 180 mg. and have an off-white color. Each tablet comprises about 2.68 mg. of clemastine fumarate.

Hardness is 5.0 kP on a Heberlein (Schleuniger) Hardness Tester, and friability on a Hoffman-Laroche Friabilator at 25 rpm for 4 minutes, is about 0.12%.

EXAMPLE 3

Tablets 1 and 2, prepared as in Examples 1 and 2 respectively, are respectively subjected to dissolution studies according to the method described in *U.S. Pharmacopoeia* (1985) Vol. XXI, pp. 1243–1244.

A multiple position dissolution stirrer such as that described at USP p. 1244, Apparatus 2, is employed, which is equipped with a Teflon paddle* in each of six vessels. A dissolution medium** comprising deaerated and distilled water is maintained at 37°±0.5° C. A tablet is sequentially dropped into each vessel. Stirring and timing (time zero) is commenced as the first tablet hits the bottom of the vessel (under the paddle).

\* The paddle is stirred at a rate of 100 rpm in the Tablet 1 dissolution study), and 50 rpm in the Tablet 2 dissolution study.
\*\* Tablet 1: 1000 ml.; Tablet 2: 900 ml.

At regular intervals, aliquots of test solution are withdrawn from each of the vessels in the order in which the tablets were originally dropped, using a stainless steel cannula. The aliquots are withdrawn from a point midway between the surface of the dissolution medium and the top of the paddle and not less than 1 cm. from each vessel wall.

The amount of medicament present in each of the vessels is calculated by reference to standard solutions using UV spectroscopy.

Figure 2:
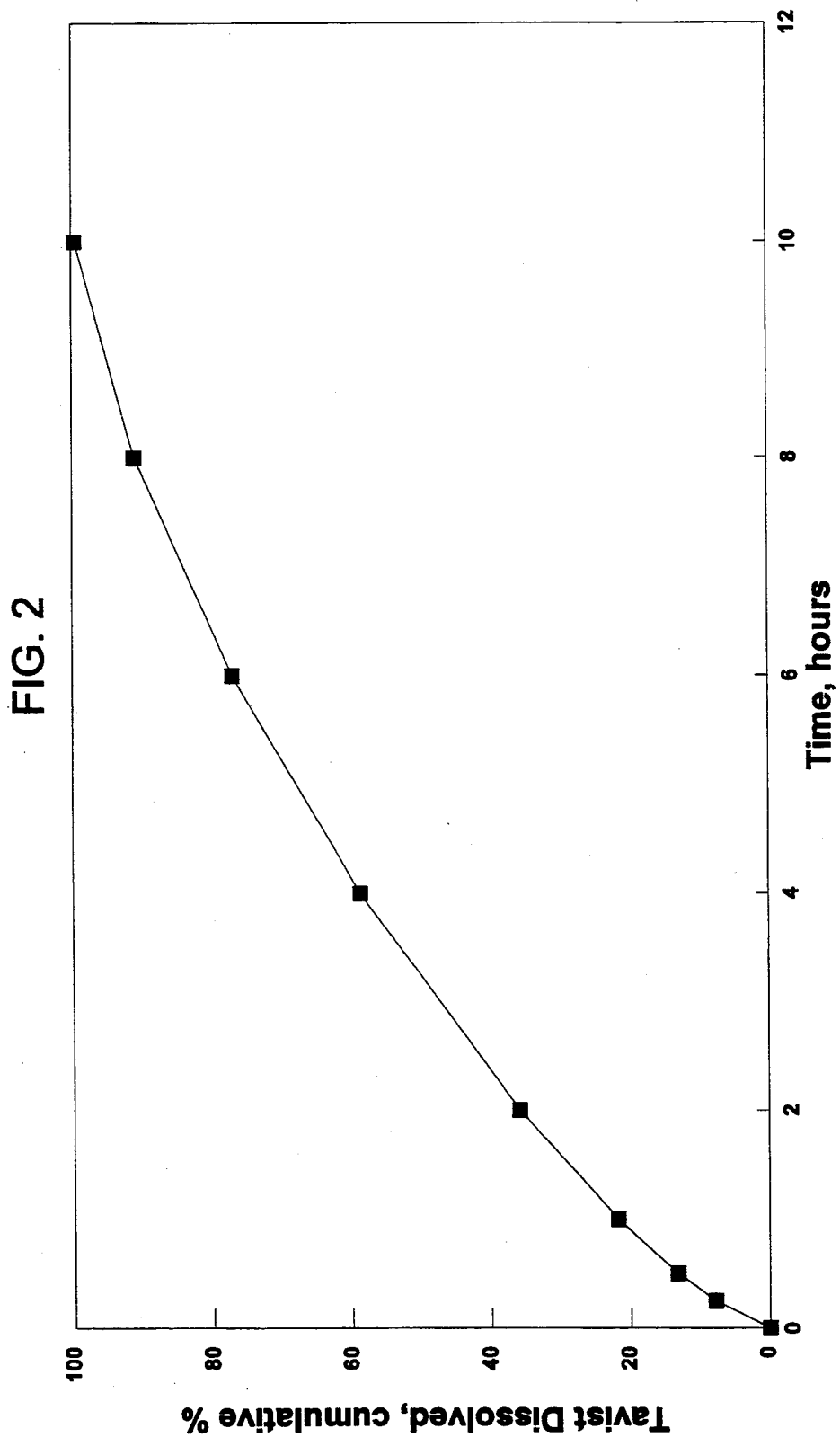

Accompanying FIGS. 1 and 2 depict the cumulative amount of medicament delivered by each of Tablets 1 and 2, respectively, over an extended period of time.

It will be seen that the tablets of the invention provide a gradual, controlled release of the medicament over an extended period of time.

What is claimed is:

1. A composition for preparing a therapeutically active sustained release dosage form which comprises a melt granulated substantially homogeneous mixture comprising:
   (A) 5 to 90 wt. % of a hydrophilic cellulose ether polymer or polymer mixture;
   (B) 5 to 50 wt. % of a granulating medium comprising polyethylene glycol and a glyceryl ester of at least one $C_{12-28}$ fatty acid, wherein said granulating medium has a melting range above about 30° C.; and
   (C) a therapeutically active medicament.

2. A composition according to claim 1 wherein the polyethylene glycol has an average molecular weight of at least about 900.

3. A composition according to claim 2 wherein the polyethylene glycol has an average molecular weight of about 3,000 to about 9,000.

4. A composition according to claim 3 wherein the polethylene glycol (PEG) is selected from the group consisting of PEG 3350, PEG 4600, PEG 8000, and mixtures thereof.

5. A composition according to claim 3 wherein the hydrophilic cellulose ether polymer is selected from the group consisting of hydroxypropylmethylcellulose, methylcellulose, hydroxypropylcellulose, hydroxyethylcellulose, sodiumcarboxymethylcellulose, carboxypolymethylene, carboxymethylhydroxyethylcellulose, and mixtures thereof.

6. A composition according to claim 5 wherein the hydrophilic cellulose ether polymer is selected from hydroxypropylmethylcellulose, methylcellulose, and mixtures thereof.

7. A composition according to claim 6 wherein the hydrophilic cellulose ether polymer comprises methylcellulose.

8. A composition according to claim 6 wherein the lipid component comprises glycerylpalmitostearate.

9. A composition according to claim 7 wherein the methylcellulose has a methoxyl content of about 27.5 to 31.5 wt. %.

10. A composition according to claim 9 wherein the methylcellulose is selected from 4,000 and 15,000 cps viscosity grades.

11. A composition according to claim 6 wherein the hydrophilic cellulose ether polymer comprises hydroxypropylmethylcellulose.

12. A composition according to claim 11 wherein the hydroxypropylmethylcellulose has a methoxyl content of about 16.5 to 30 wt. % and a hydroxypropoxyl content of about 4 to 32 wt. %.

13. A composition according to claim 11 wherein the hydroxypropylmethylcellulose is selected from 100, 4,000, 15,000 and 100,000 cps grades of hydroxypropylmethylcellulose having a methoxyl content of 19-24 wt. % and a hydroxypropoxyl content of 7-12 wt. %.

14. A composition according to claim 11 wherein the hydroxypropylmethylcellulose is a 4,000 cps grade having a 28-30 wt. % methoxyl content and a 7-12 wt. % hydroxypropoxyl content.

15. A composition according to claims 1 or 5 comprising:
   (A) 30 to 40 wt. % of hydrophilic cellulose ether polymer or polymer mixture;
   (B) 15 to 30 wt. % of a granulating medium comprising:
      (i) 5 to 20 wt. % polyethylene glycol;
      (ii) 5 to 20 wt. % of a glyceryl ester of at least one $C_{12-28}$ fatty acid; and
   (C) a therapeutically active medicament.

16. A composition for preparing a therapeutically active sustained release solid unit dosage form which comprises a melt granulated substantially homogeneous mixture comprising:
   (A) 30 to 40 wt. % of hydroxypropylmethylcellulose polymer;
   (B) 15 to 30 wt. % of a granulating medium, which comprises:
      (i) 5 to 20 wt. % of glyceryl esters of $C_{12-28}$ fatty acids, and
      (ii) 5 to 20 wt. % of polyethylene glycol having an average molecular weight of about 3,000 to about 9,000

(weight percents based on total composition),
      wherein said granulating medium has a melting range of about 30°-100° C.; and
   (C) a therapeutically active medicament.

17. A composition according to claim 16 wherein the polethylene glycol (PEG) is selected from the group consisting of PEG 3350, PEG 4600, PEG 8000, and mixtures thereof.

18. A composition according to claim 17 wherein the hydroxypropylmethylcellulose is selected from 100, 4,000, 15,000 and 100,000 cps grades of hydroxypropylmethylcellulose having a methoxyl content of about 19-24 wt. % and a hydropropoxyl content of about 7-12 wt. %.

19. A composition according to claim 18 wherein the glyceryl ester is glycerylpalmitostearate.

20. A composition according to claim 16 wherein the granulating medium has a melting range of 50°-100° C.

21. A process for preparing a therapeutically active composition which comprises:
   (a) forming a molten mass by applying heat to a composition comprising:
      (A) 5 to 90 wt. % of a hydrophilic cellulose ether polymer or mixtures thereof;
      (B) 5 to 50 wt. % of a granulating medium comprising polyethylene glycol and glyceryl esters of $C_{12-28}$ fatty acids, wherein the granulating medium has a melting range above about 30° C.; and
      (C) a therapeutically active medicament,
   (b) mixing the mass to provide a substantially homogeneous mixture; and
   (c) cooling the mixture to room temperature.

22. A process according to claim 21 wherein the granulating medium has a melting range of 50°-100° C.

23. A composition according to claims 1, 6 or 16 in tableted form.

* * * * *